(12) United States Patent
Hermes et al.

(10) Patent No.: US 10,347,848 B2
(45) Date of Patent: Jul. 9, 2019

(54) AMORPHOUS MATERIAL AND THE USE THEREOF

(71) Applicant: BASF SE, Ludwigshafen (DE)

(72) Inventors: Wilfried Hermes, Karlsruhe (DE); Ingmar Bruder, Neuleiningen (DE); Peter Erk, Frankenthal (DE); Daniel Waldmann, Lambsheim (DE)

(73) Assignee: BASF SE, Ludwigshafen (DE)

( * ) Notice: Subject to any disclaimer, the term of this patent is extended or adjusted under 35 U.S.C. 154(b) by 195 days.

(21) Appl. No.: 14/916,523

(22) PCT Filed: Sep. 2, 2014

(86) PCT No.: PCT/EP2014/068602
§ 371 (c)(1),
(2) Date: Mar. 3, 2016

(87) PCT Pub. No.: WO2015/032748
PCT Pub. Date: Mar. 12, 2015

(65) Prior Publication Data
US 2016/0218302 A1 Jul. 28, 2016

(30) Foreign Application Priority Data
Sep. 3, 2013 (EP) .................................. 13182862

(51) Int. Cl.
*C07C 211/65* (2006.01)
*H01L 51/00* (2006.01)
(Continued)

(52) U.S. Cl.
CPC ........ *H01L 51/0077* (2013.01); *C07C 209/60* (2013.01); *C07C 211/04* (2013.01);
(Continued)

(58) Field of Classification Search
CPC .................................................... C07C 211/65
See application file for complete search history.

(56) References Cited

U.S. PATENT DOCUMENTS 2,761,791 A 9/1956 Russell
5,871,579 A 2/1999 Liang et al.
(Continued)

FOREIGN PATENT DOCUMENTS

JP 7-249790 9/1995
WO 00/70655 11/2000
(Continued)

OTHER PUBLICATIONS

Aswani Yella, et al.,"Porphyrin-Sensitized Solar Cells with Cobalt (II/III)-Based Redox Electrolyte Exceed 12 Percent Efficiency," Science Magazine, vol. 334, 2011, 8 pages.
(Continued)

*Primary Examiner* — Magali P Slawski
(74) *Attorney, Agent, or Firm* — Oblon, McClelland, Maier & Neustadt, L.L.P.

(57) ABSTRACT

The present invention relates to a new amorphous material with advantageous properties as charge transport material and/or absorber material for various applications, in particular in photoelectric conversion devices, i.e. an amorphous material of the composition $(R^1NR^2_3)_5Me\ X^1_aX^2_b$ wherein $R^1$ is $C_1$-$C_4$-alkyl, $R^2$ are independently of one another hydrogen or $C_1$-$C_4$-alkyl, Me is a divalent metal, $X^1$ and $X^2$ have different meanings and are independently of one another selected from F, Cl, Br, I or a pseudohalide, a and b are independently of one another 0 to 7, wherein the sum of a and b is 7.

29 Claims, 3 Drawing Sheets (51) Int. Cl.
    *H01L 51/42* (2006.01)
    *C07C 209/60* (2006.01)
    *C07C 211/04* (2006.01)
    *H01L 27/28* (2006.01)
    *H01L 33/50* (2010.01)
    *B82Y 30/00* (2011.01)
    *H01L 51/05* (2006.01)
    *H01L 51/50* (2006.01)
    *H01L 27/30* (2006.01)

(52) U.S. Cl.
    CPC ............ *C07C 211/65* (2013.01); *H01L 27/28* (2013.01); *H01L 33/502* (2013.01); *H01L 51/422* (2013.01); *H01L 51/424* (2013.01); *H01L 51/4213* (2013.01); *B82Y 30/00* (2013.01); *H01L 27/302* (2013.01); *H01L 51/0558* (2013.01); *H01L 51/5012* (2013.01); *Y02E 10/549* (2013.01)

(56) References Cited

U.S. PATENT DOCUMENTS

| | | | |
|---|---|---|---|
| 5,882,548 A | | 3/1999 | Liang et al. |
| 5,882,549 A | | 3/1999 | Zuber et al. |
| 2007/0213542 A1* | | 9/2007 | Van Der Heide ..... C07C 29/128 549/229 |
| 2008/0115829 A1 | | 5/2008 | Lee et al. |
| 2008/0299205 A1* | | 12/2008 | Mayer ...................... A61K 8/85 424/489 |
| 2011/0136905 A1* | | 6/2011 | Cabri ................... C07C 275/16 514/551 |
| 2014/0011243 A1* | | 1/2014 | Brockmann ......... C12N 9/1051 435/101 |
| 2016/0122186 A1* | | 5/2016 | Jafari ..................... B01D 53/02 95/136 |
| 2017/0200608 A1* | | 7/2017 | Guo .................. H01L 21/02667 |
| 2017/0217850 A1* | | 8/2017 | Braje ..................... C07B 63/04 |
| 2017/0341069 A1* | | 11/2017 | Lipshutz ................. C07C 45/68 |

FOREIGN PATENT DOCUMENTS

| | | |
|---|---|---|
| WO | 02/101838 A1 | 12/2002 |
| WO | 2005/019373 A2 | 3/2005 |
| WO | 2009/013282 A1 | 1/2009 |
| WO | WO 2013/126385 | 8/2013 |
| WO | WO 2013/126537 | 8/2013 |

OTHER PUBLICATIONS

Hui-Seon Kim, et al., "Lead Iodide Perovskite Sensitized All-Solid-State Submicron Thin Film Mesoscopic Solar Cell with Efficiency Exceeding 9%," Scientific Reports, vol. 2, 2012, 7 pages.

Michael M. Lee, et al., "Efficient Hybrid Solar Cells Based on Meso-Superstructured Organometal Halide Perovskites," Science Magazine, vol. 338, 2012, 6 pages.

Edoardo Mosconi, et al., "First-Principles Modeling of Mixed halide Organometal Perovskites for Photovoltaic Applications", The Journal of Physical Chemistry, PN160527, American Chemical Society, 2013, 117, pp. 13902-13913.

Constantinos C. Stoumpos, et al., "Semiconducting Tin and Lead Iodide Perovskites with Organic Cations: Phase Transitions, High Mobilities, and Near-Infrared Photoluminescent Properties", Inorganic Chemistry, American Chemical Society, 2013,52, pp. 9019-9038.

George C. Papavassiliou, et al., "Excitonic Bands in the Spectra of Some Organic-Inorganic Hybrid Compounds Based on Metal Halide Units," *Monatshefte fur Chemie*, 132, pp. 113-119 (2001).

* cited by examiner

AMORPHOUS MATERIAL AND THE USE THEREOF

FIELD OF THE INVENTION

The present invention relates to a new amorphous material with advantageous properties as charge transport material and/or absorber material for various applications, in particular in photoelectric conversion devices.

Dye-sensitized photoelectric conversion elements (dye-sensitized solar cells, DSCs) have attracted much attention in recent years. They have several advantages compared to silicon-based solar cells such as lower production and material costs because an inexpensive metal oxide semiconductor such as titanium dioxide can be used therefore without purification to a high purity. Other advantages include their flexibility, transparency and light weight. The overall performance of a photoelectric conversion device is characterized by several parameters such as the open circuit voltage ($V_{oc}$), the short circuit current ($I_{sc}$), the fill factor (FF) and the energy conversion efficiency ($\eta$) resulting therefrom. Dye-sensitized solar cells are one of the most efficient alternative solar cell technologies at present. There is still an ongoing need to further improve the performance of solid dye-sensitized photoelectric conversion devices, in particular their energy conversion efficiency $\eta$.

The construction of a DSC is generally based on a transparent substrate (e.g. glass), which is coated with a transparent conductive layer, the working electrode. An n-conductive metal oxide is generally applied to this electrode or in the vicinity thereof, for example a nanoporous titanium dioxide layer ($TiO_2$) of approx. 2-20 μm thickness. On the surface thereof, in turn, a monolayer of a light-sensitive dye, for example a ruthenium complex or an organic dye, is typically adsorbed, which can be converted to an excited state by light absorption. The counter electrode may optionally have a catalytic layer of a metal, for example platinum, with a thickness of a few μm. The function of the DSC is based on the fact that light is absorbed by the dye, and electrons are transferred from the excited dye to the n-semiconductive metal oxide semiconductor and migrate thereon to the anode. In liquid DSC the area between the two electrodes is filled with a redox electrolyte, for example a solution of iodine ($I_2$) and lithium iodide (LiI), which ensures that a photocurrent can be collected at the front and back contacts of the cell.

In a liquid variant of the DSCs, efficiencies of over 12% have been reported (e.g. Grätzel et al., Science 2011, 334, 629-634). Nevertheless, cells comprising a liquid electrolyte have specific disadvantages that prevent a wider use of this technology. Thus, in many cases liquid DSC suffers from durability problems that result from their use of organic liquid electrolytes which cause serious problems, such as electrode corrosion and electrolyte leakage. Therefore, suitable replacements that can be used for hole conduction in lieu of a liquid electrolyte have been searched for. Various materials have therefore been studied for their suitability as solid electrolytes/p-semiconductors.

A new development in the production of solid DSC is the use of organometallic Perovskites as light harvesting compounds (Perovskite sensitized solar cells, PSCs). H.-S. Kim et al. describe in Scientific Reports, 2: 59, DOI: 10.1038/srep00591 lead iodide Perovskite-sensitized solar cells with an efficiency exceeding 9%. In those cells, Perovskite nanoparticles of methyl ammonium lead iodide are used as absorber material in combination with mesoporous $TiO_2$ as transparent n-type semiconductor and spiro-MeOTAD as p-type hole conductor.

M. M. Lee, J. Teuscher, T. Miyasaki, T. N. Murakami and H. J. Snaith describe in Sciencexpress, 4 Oct. 2012, 10.1126/science.1228604 hybrid solar cells based on methylammonium lead iodide chloride ($CH_3NH_3PbI_2Cl$) as crystalline Perovskite absorber material. In those cells mesoporous alumina is used instead of titanium dioxide. In those cells $Al_2O_3$ does not act as n-type oxide but as a meso-scale "scaffold" upon which the device is structured. Therefore the authors no longer denote the devices as "sensitized" solar cells but as a two-component hybrid solar cells or "meso-superstructured solar cells".

It is an object of the present invention to provide new compounds which can be used advantageously for transporting electronic charge and/or as absorber material in diverse fields. In particular the new compounds should be suitable for the preparation of photoelectric conversion devices. Further, the material should be easy to process, e.g. by a film building process.

It was now surprisingly found that this object is achieved by the new amorphous materials of the invention.

SUMMARY OF THE INVENTION

According to a first aspect of the present invention there is provided an amorphous material of the composition $(R^1NR^2{}_3)_5MeX^1{}_aX^2{}_b$ wherein
$R^1$ is $C_1$-$C_4$-alkyl,
$R^2$ are independently of one another hydrogen or $C_1$-$C_4$-alkyl,
Me is a divalent metal,
$X^1$ and $X^2$ have different meanings and are independently of one another selected from F, Cl, Br, I or a pseudohalide,
a and b are independently of one another 0 to 7, wherein the sum of a and b is 7.

A preferred embodiment is an amorphous material of the composition $(CH_3NH_3)_5PbI_{3.5}Cl_{3.5}$ or $(CH_3NH_3)_5SnI_{3.5}Cl_{3.5}$.

A further object of the present invention relates to a composition comprising an amorphous material as defined above and in the following and at least one different component.

A further object of the present invention relates to a process for the preparation of an amorphous material of the composition $(R^1NR^2{}_3)_5MeX^1{}_aX^2{}_b$ wherein
$R^1$ is $C_1$-$C_4$-alkyl,
$R^2$ are independently of one another hydrogen or $C_1$-$C_4$-alkyl,
Me is a divalent metal,
$X^1$ and $X^2$ have different meanings and are independently of one another selected from F, Cl, Br, I or a pseudohalide,
comprising reacting
a compound of the formula $(R^1NR^2{}_3)X^1$,
a compound of the formula $(R^1NR^2{}_3)X^2$ and
a compound of the formula $MeX^2{}_2$, at an elevated temperature in the melt or the presence of a solvent.

A further object of the present invention relates to a photoelectric conversion device comprising at least one amorphous material as defined above and in the following or a composition comprising such a material.

BRIEF DESCRIPTION OF THE SEVERAL VIEWS OF THE DRAWINGS

At 140° C., a clear yellow-colored melt without solid contents was obtained.

A special embodiment is a photoelectric conversion device, comprising:
an electrically conductive layer being part of or forming the working electrode (anode),
a photosensitive layer comprising an absorber material and optionally comprising a semi-conductive metal oxide (which can act as electron transfer material) or an insulating material (which can act as a scaffold),
a charge transfer layer,
an electrically conductive layer being part of or forming the counter electrode (cathode),
wherein the photosensitive layer and/or the charge transfer layer comprises at least one amorphous material as defined above and in the following or a composition comprising such a material.

A further object of the present invention relates to a solar cell comprising the photoelectric conversion device of the invention.

A further object of the present invention relates to a field-effect transistor (FET), comprising a substrate having at least one gate structure, a source electrode and a drain electrode and at least one amorphous material as defined herein or a composition, comprising such a material, as defined herein.

A further object of the present invention relates to a substrate comprising a plurality of field-effect transistors (FETs), at least some of the field-effect transistors comprising at least one amorphous material as defined herein or a composition, comprising such a material, as defined herein.

A further object of the present invention relates to an electroluminescent arrangement comprising an upper electrode, a lower electrode, wherein at least one of said electrodes is transparent, an electroluminescent layer and optionally an auxiliary layer, wherein the electroluminescent arrangement comprises at least one amorphous material as defined herein or a composition, comprising such a material, as defined herein. In particular, the electroluminescent arrangement is a light-emitting diode (LED).

A further object of the present invention relates to the use of an amorphous material as defined above and in the following or a composition comprising such a material as or in the semiconducting layer of a thin film transistor (TFT), as or in the semiconducting layer of a light-emitting diode (LED), as or in the phosphor material of an LED, as charge transport material in batteries, rechargeable batteries (accumulators), etc.

DETAILED DESCRIPTION OF THE INVENTION

In an alternative notation the amorphous material can be described as $$5(R^1NR^2{}_3):1Me:aX^1:bX^2.$$

In the context of the invention, the expression "amorphous material" denotes a material that (like glass) does not produce sharp diffraction peaks in the X-ray powder diffraction (XRD).

The expression "halogen" denotes in each case fluorine, bromine, chlorine or iodine, particularly chlorine, bromide or iodine.

Suitable pseudohalides are e.g. CN, SCN, OCN, $N_3$, etc.

Suitable $C_1$-$C_4$-alkyl groups are especially methyl, ethyl, n-propyl, isopropyl, n-butyl, isobutyl, sec-butyl or tert-butyl.

Preferably, $R^1$ is methyl or ethyl. In particular, $R^1$ is methyl.

Preferably, the $R^2$ groups are all hydrogen.

Preferably, Me is selected from Pb, Sn, Fe, Zn, Cd, Co, Cu, Ni, Mn and mixtures thereof. More preferably, Me is selected from Pb, Sn and mixtures thereof. In particular, Me is Pb.

In a preferred embodiment of the amorphous material according to the invention $X^1$ is I and $X^2$ is Cl.

Preferably, a and b are both 0.1 to 6.9, more preferably 0.5 to 6.5, in particular 1 to 6. In a preferred embodiment of the amorphous material according to the invention a and b are both 3.5.

A special embodiment is an amorphous material of the composition $$(CH_3NH_3)_5PbI_{3.5}Cl_{3.5} \text{ or } (CH_3NH_3)_5SnI_{3.5}Cl_{3.5}.$$

A further object of the present invention relates to a composition comprising an amorphous material as defined above and in the following and at least one different component. Suitable further components are amorphous or crystalline components, in particular on the basis of at least some of the elements present in the amorphous material of the invention.

A further object of the present invention relates to a process for the preparation of an amorphous material of the composition $$(R^1NR^2{}_3)_5MeX^1{}_aX^2{}_b$$

wherein
$R^1$ is $C_1$-$C_4$-alkyl,
$R^2$ are independently of one another hydrogen or $C_1$-$C_4$-alkyl,
Me is a divalent metal,
$X^1$ and $X^2$ have different meanings and are independently of one another selected from F, Cl, Br, I or a pseudohalide,
comprising reacting
a compound of the formula $(R^1NR^2{}_3)X^1$,
a compound of the formula $(R^1NR^2{}_3)X^2$ and
a compound of the formula $MeX^2{}_2$,
at an elevated temperature in the melt or the presence of a solvent.

Preferably, the components are mixed in a ratio that corresponds to the stoichiometric amount of the elements in the composition $$5(R^1NR^2{}_3):1Me:aX^1:bX^2.$$

In a special embodiment the molar ratios of $(R^1NR^2{}_3)X^1$: $(R^1NR^2{}_3)X^2$:$MeX^2{}_2$ are about 3.5:1.5:1.

In a first embodiment the reaction is performed in the melt. According to this embodiment the reaction mixture is heated to a temperature above the melting point of the educt composition. If the reaction is performed in the melt the temperature is preferably in a range of from 60 to 250° C., more preferably 80 to 200° C.

In a second embodiment the reaction is performed in the presence of a solvent. Suitable solvents are aprotic solvent. Suitable aprotic solvents are dimethylformamide, ethers, such as dioxane and diglyme (bis(2-methoxyethyl) ether), N-methylpyrrolidone, $(CH_3)_2SO$, dimethyl sulfone, sulfolane, cyclic ureas such as 1,3-dimethyl-3,4,5,6-tetrahydro-2 (1H)-pyrimidinone (DMPU), imidazolidin-2-one, acetonitrile, methoxyaceto-nitrile or mixtures thereof. If the reaction is performed in the presence of a solvent the temperature is preferably in a range of from 20 to 200° C., more preferably 40 to 100° C.

In a preferred embodiment, the reaction is performed under an inert gas atmosphere. Suitable inert gases are for example nitrogen or argon.

A further object of the present invention relates to a photoelectric conversion device. Preferably, the photoelectric conversion device is a thin film photoelectric conversion device.

As mentioned before, a special embodiment is a photoelectric conversion device, comprising:
an electrically conductive layer being part of or forming the working electrode (anode),
a photosensitive layer comprising an absorber material and optionally comprising a semiconductive metal oxide (which can act as electron transfer material) or an insulating material (which can act as a scaffold),
a charge transfer layer,
an electrically conductive layer being part of or forming the counter electrode (cathode),
wherein the photosensitive layer and/or the charge transfer layer comprises at least one amorphous material as defined above and in the following or a composition comprising such a material.

In a preferred embodiment, the photosensitive layer comprises at least one amorphous material as defined above and in the following or a composition comprising such a material as absorber material. According to this embodiment it is not necessary that the photosensitive layer additionally comprises a semiconductive metal oxide or an insulating material.

It is also possible that in this embodiment the charge transfer layer comprises at least one amorphous material according to the invention.

In a further preferred embodiment, the photosensitive layer comprises at least one Perovskite material as absorber material. In this embodiment the photosensitive layer may additionally comprise at least one amorphous material as defined above and in the following or a composition comprising such a material.

It is also possible that in this embodiment the charge transfer layer does comprise at least one amorphous material according to the invention.

The absorber material can be deposited on a semiconductive metal oxide or an insulating material, e.g. an insulating metal oxide. Suitable semiconductive metal oxides are those know for the use in dye-sensitized photoelectric conversion devices, in particular $TiO_2$. A suitable insulating metal oxide that does not act as a n-type oxide is $Al_2O_3$.

In a further preferred embodiment the photoelectric conversion device according to the invention additionally comprises a hole-conducting layer between the charge transfer layer and the cathode. Suitable materials employed in the hole-conducting layer are e.g. 2,2',7,7'-tetrakis(N,N-di-p-methoxyphenyl-amine)-9,9'-spirobifluorene ("spiro-MeO-TAD").

A suitable process for producing a photoelectric conversion device comprises the following steps:
i) providing an electrically conductive layer;
ii) optionally depositing an undercoating layer thereon,
iii) depositing a photosensitive layer on the electrically conductive layer obtained in step i) or, if present, the undercoating layer obtained in step ii);
iv) depositing a charge transfer layer on the photosensitive layer obtained in step iii); and
v) depositing a counter electrically conductive layer on the charge transfer layer obtained in step iv).

The photosensitive layer and/or the charge transfer layer comprises at least one amorphous material as defined above and in the following or a composition comprising such a material.

The electrically conductive layer and/or the counter electrically conductive layer may be disposed on a substrate (also called support or carrier) to improve the strength of the photoelectric conversion device. In the present context, a layer composed of the electrically conductive layer and a substrate on which it is disposed is referred to as conductive support. A layer composed of the counter electrically conductive layer and a substrate on which it is optionally disposed is referred to as counter electrode. Preferably, the electrically conductive layer and the substrate on which it is optionally disposed are transparent. The counter electrically conductive layer and optionally also the support on which this is optionally disposed may be transparent too, but this is not critical.

Each layer comprised in the photoelectric conversion device of the present invention will be explained in detail below.

(A) Electrically Conductive Layer [Step (i)]

The electrically conductive layer is either as such stable enough to support the remaining layers, or the electrically conductive material forming the electrically conductive layer is disposed on a substrate (also called support or carrier). Preferably, the electrically conductive material forming the electrically conductive layer is disposed on a substrate. The combination of electrically conductive material disposed on a substrate is called in the following "conductive support".

In the first case, the electrically conductive layer is preferably made of a material that has a sufficient strength and that can sufficiently seal the photoelectric conversion device, for example, a metal such as platinum, gold, silver, copper, zinc, titanium, aluminum and an alloy composed thereof.

In the second case, the substrate on which the electrically conductive layer containing an electrically conductive material is generally disposed opposite of the photosensitive layer, so that the electrically conductive layer is in direct contact with the photosensitive layer.

Preferred examples of the electrically conductive material include: metals such as platinum, gold, silver, copper, zinc, titanium, aluminum, indium and alloys composed thereof; carbon, especially in the form of carbon nano tubes; and electrically conductive metal oxides, especially transparent conductive oxides (TCO), such as for example indium-tin composite oxides, tin oxides doped with fluorine, antimony or indium and zinc oxide doped with aluminum. In case of metals, these are generally used in form of thin films, so that they form a sufficiently transparent layer. More preferably, the electrically conductive material is selected from transparent conductive oxides (TCO). Among these, tin oxides doped with fluorine, antimony or indium and indium-tin oxide (ITO) are preferred, more preferred being tin oxides doped with fluorine, antimony or indium and specifically preferred being tin oxides doped with fluorine. Specifically, the tin oxide is $SnO_2$.

The electrically conductive layer preferably has a thickness of 0.02 to 10 μm and more preferably from 0.1 to 1 μm.

Generally, light will be irradiated from the side of the electrically conductive layer (and not from the counter electrically conductive layer side). Thus, as already mentioned, it is preferred that the support which carries the electrically conductive layer and preferably the conductive support as a whole is substantially transparent. Herein, the term "substantially transparent" means that the light transmittance is 50% or more to a light in visible region to near infrared region (400 to 1000 nm). The light transmittance is preferably 60% or more, more preferably 70% or more and in particular 80% or more. The conductive support particularly preferably has high light transmittance to a light that the photosensitive layer has sensitivity to.

The substrate may be made of a glass, such as soda glass (that is excellent in strength) and non-alkali glass (that is not affected by alkaline elution). Alternatively, a transparent polymer film may be used as substrate. Used as the materials for the polymer film may be tetraacetyl cellulose (TAC), polyethylene terephthalate (PET), polyethylene naphthalate (PEN), syndiotactic polystyrene (SPS), polyphenylenesulfide (PPS), polycarbonate (PC), polyarylate (PAr), polysulfone (PSF), polyestersulfone (PES), polyimide (PI), polyetherimide (PEI), cyclic polyolefin, brominated phenoxy resin, and the like.

The conductive support is preferably prepared by disposing the electrically conductive material on the substrate by means of liquid coating or vapor deposition.

The amount of the electrically conductive material to be disposed on the substrate is chosen so that a sufficient transparency is secured. The suitable amount depends on the conductive material and the substrate used and will be determined for the single cases. For instance, in case of TCOs as conductive material and glass as substrate the amount may vary from 0.01 to 100 g per 1 $m^2$.

It is preferable that a metal lead is used to reduce the resistance of the conductive support. The metal lead is preferably made of a metal such as platinum, gold, nickel, titanium, aluminum, copper, silver, etc. It is preferable that the metal lead is provided on the substrate by a vapor deposition method, a sputtering method or the like, the electrically conductive layer being disposed thereon. The reduction in incident light quantity owing to the metal lead is limited to preferably 10% or less, more preferably 1 to 5% or less.

(B) Undercoating Layer ("Buffering Layer") [Optional Step (ii)]

The layer obtained in step (i) may be coated with a buffering layer. The purpose is to avoid a direct contact of the charge transfer layer with the electrically conductive layer and thus to prevent short-circuits, particularly in the case where the charge transfer layer is a solid hole-transporting material.

This "undercoating" or buffering layer material is preferably a metal oxide. The metal oxide is preferably selected from a titanium, tin, zinc, iron, tungsten, vanadium or niobium oxide, such as $TiO_2$, $SnO_2$, $Fe_2O_3$, $WO_3$, ZnO, $V_2O_5$ or $Nb_2O_5$, and is more preferably $TiO_2$.

The undercoating layer may be disposed e.g. by a spray-pyrolysis method as described for example in Electrochim. Acta, 40, 643 to 652 (1995), or a sputtering method as described for example in Thin Solid Films 445, 251-258 (2003), Surf. Coat. Technol. 200, 967 to 971 (2005) or Coord. Chem. Rev. 248 (2004), 1479.

The thickness of the undercoating layer is preferably 5 to 1000 nm, more preferably 10 to 500 nm and in particular 10 to 200 nm.

(C) Photosensitive Layer [Step (iii)]

In a first preferred embodiment, the photosensitive layer comprises at least one amorphous material according to the invention or a composition comprising such a material. In this embodiment, it is not necessary that the photosensitive layer additionally comprises a semiconductive metal oxide or an insulating material.

In a second preferred embodiment, the photosensitive layer comprises at least one Perovskite material as absorber material and a semiconductive metal oxide or a carrier material that does not act as an n-type oxide. In this embodiment, the photosensitive layer and/or the charge transfer layer (see (D) below) comprises at least one amorphous material according to the invention or a composition comprising such a material.

(1) Semiconductive Metal Oxide

An n-type semiconductor is preferably used in the present invention, in which conduction band electrons act as a carrier under photo-excitation condition to provide anode current.

Suitable semiconductive metal oxides are generally all metal oxides known to be useful on organic solar cells. They include: oxides of titanium, tin, zinc, iron, tungsten, zirconium, hafnium, strontium, indium, cerium, yttrium, lanthanum, vanadium, caesium, niobium or tantalum. Further, composite semiconductors such as $M^1{}_xM^2{}_yO_z$ may be used in the present invention, wherein M, $M^1$ and $M^2$ independently represent a metal atom, O represents an oxygen atom, and x, y and z represent numbers combined with each other to form a neutral molecule. Examples are $TiO_2$, $SnO_2$, $Fe_2O_3$, $WO_3$, ZnO, $Nb_2O_5$, $SrTiO_3$, $Ta_2O_5$, $Cs_2O$, zinc stannate, complex oxides of the Perovskite type, such as barium titanate, and binary and ternary iron oxides.

Preferred semiconductive metal oxides are selected from $TiO_2$, $SnO_2$, $Fe_2O_3$, $WO_3$, ZnO, $Nb_2O_5$, and $SrTiO_3$. Of these semiconductors, more preferred are $TiO_2$, $SnO_2$, ZnO and mixtures thereof. Even more preferred are $TiO_2$, ZnO and mixtures thereof, particularly preferred being $TiO_2$.

The metal oxides are preferably present in amorphous or nanocrystalline form. More preferably, they are present as nanocrystalline porous layers. The metal oxide layers may also be present in a structured form, such as nanorods.

If more than one metal oxide is used, the two or more metal oxides can be applied as mixtures when the photosensitive layer is formed. Alternatively, a layer of a metal oxide may be coated with one or more metal oxides different therefrom.

The metal oxides may also be present as a layer on a semiconductor different therefrom, such as GaP, ZnP or ZnS.

$TiO_2$ and ZnO used in the present invention are preferably in anatase-type crystal structure, which in turn is preferably nanocrystalline.

The semiconductor may or may not comprise a dopant to increase the electron conductivity thereof. Preferred dopants are metal compounds such as metals, metal salts and metal chalcogenides.

In the photosensitive layer the semiconductive metal oxide layer is preferably porous, particularly preferably nanoporous and specifically mesoporous.

Porous material is characterized by a porous, non-smooth surface. Porosity is a measure of the void spaces in a material, and is a fraction of the volume of voids over the total volume. Nanoporous material has pores with a diameter in the nanometer range, i.e. ca. from 0.2 nm to 1000 nm, preferably from 0.2 to 100 nm. Mesoporous material is a specific form of nanoporous material having pores with a diameter of from 2 to 50 nm. "Diameter" in this context refers to the largest dimension of the pores. The diameter of the pores can be determined by several porosimetry methods, such as optical methods, imbibition methods, water evaporation method, mercury intrusion porosimetry or gas expansion method.

The particle size of the semiconductive metal oxide used for producing the semiconductive metal oxide layer is generally in the nm to μm range. The mean size of primary semiconductor particles, which is obtained from a diameter of a circle equivalent to a projected area thereof, is preferably 200 nm or less, e.g. 5 to 200 nm, more preferably 100 nm or less, e.g. 5 to 100 nm or 8 to 100 nm.

Two or more of the semiconductive metal oxides having a different particle size distribution may be mixed in the preparation of the photosensitive layer. In this case, the average particle size of the smaller particles is preferably 25 nm or less, more preferably 10 nm or less. To improve a light-capturing rate of the photoelectric conversion device by scattering rays of incident light, the semiconductive metal oxides having a large particle size, e.g. approximately 100 to 300 nm in diameter, may be used for the photosensitive layer.

Preferred as a method for producing the semiconductive metal oxides are: sol-gel methods described for example in Materia, Vol. 35, No. 9, Page 1012 to 1018 (1996). A method which comprises preparing oxides by subjecting chlorides to a high temperature hydrolysis in an oxyhydrogen salt is also preferred.

In the case of using titanium oxide as the semiconductive metal oxides, the above-mentioned sol-gel methods, gel-sol methods, high temperature hydrolysis methods are preferably used. Of the sol-gel methods, also preferred are such that described in Barbé et al., Journal of American Ceramic Society, vol. 80, no. 12, page 3157 to 3171 (1997) and Burnside et al., Chemistry of Materials, vol. 10, no. 9, page 2419 to 2425 (1998).

The semiconductive metal oxides may be applied onto the layer obtained in step (i) or, if carried out, step (ii), by: a method where the layer obtained in step (i) or (ii) is coated with a dispersion or a colloidal solution containing the particles; the above-mentioned sol-gel method; etc. A wet type layer formation method is relatively advantageous for the mass production of the photoelectric conversion device, for improving the properties of the semiconductive metal oxide dispersion, and for improving the adaptability of the layer obtained in step (i) or (ii), etc. As such a wet type layer formation method, coating methods, printing methods, electrolytic deposition methods and electrodeposition techniques are typical examples. Further, the semiconductive metal oxide layer may be disposed by: oxidizing a metal; an LPD (liquid phase deposition) method where a metal solution is subjected to ligand exchange, etc.; a sputtering method; a PVD (physical vapor deposition) method; a CVD (chemical vapour deposition) method; or an SPD (spray pyrolysis deposition) method where a thermal decomposition-type metal oxide precursor is sprayed on a heated substrate to generate a metal oxide.

The dispersion containing the semiconductive metal oxides may be prepared by: the sol-gel methods mentioned above; crushing the semiconductor in a mortar; dispersing the semiconductor while grinding it in a mill; synthesizing and precipitating the semiconductive metal oxides in a solvent; etc.

As a dispersion solvent, water or organic solvents such as methanol, ethanol, isopropyl alcohol, citronellol, terpineol, dichloromethane, acetone, acetonitrile, ethyl acetate, etc., mixtures thereof and mixtures of one or more of these organic solvents with water may be used. A polymer such as polyethylene glycol, hydroxyethylcellulose and carboxymethylcellulose, a surfactant, an acid, a chelating agent, etc. may be used as a dispersing agent, if necessary. In particular, polyethylene glycol may be added to the dispersion because the viscosity of the dispersion and the porosity of the semiconductive metal oxide layer can be controlled by changing the molecular weight of the polyethylene glycol, and the semiconductive metal oxide layer containing polyethylene glycol is hardly peeled off.

Preferred coating methods include e.g. roller methods and dip methods for applying the semi-conductive metal oxide, and e.g. air-knife methods and blade methods for calibrating the layer. Further, preferable as a method where the application and calibration can be performed at the same time are wire-bar methods, slide-hopper methods, e.g. such as described in U.S. Pat. No. 2,761,791, extrusion methods, curtain methods, etc. Furthermore, spin methods and spray methods may be used. As to wet type printing methods relief printing, offset printing, gravure printing, intaglio printing, gum printing, screen printing, etc. are preferred. A preferable layer formation method may be selected from these methods in accordance with the viscosity of the dispersion and the desired wet thickness.

The semiconductive metal oxide layer is not limited to a single layer. Dispersions each comprising the semiconductive metal oxides having a different particle size may be subjected to a multi-layer coating. Further, dispersions each containing different kinds of semiconductive metal oxides, binder or additives may be subjected to a multi-layer coating. The multi-layer coating is also effectively used in case the thickness of a single layer is insufficient.

Generally, with increasing thickness of the semiconductive metal oxide layer, which equals the thickness of the photosensitive layer, the amount of the absorber, for example the Perovskite, incorporated therein per unit of projected area increases resulting in a higher light capturing rate. However, because the diffusion distances of the generated electrons also increase, higher loss rates owing to recombination of the electric charges is to be expected. The preferred thickness of the semiconductive metal oxide layer is 0.1 to 100 μm, more preferably 0.1 to 50 μm, even more preferably 0.1 to 30 μm, in particular 0.1 to 20 μm and specifically 0.5 to 3 μm.

A coating amount of the semiconductive metal oxides per 1 $m^2$ of the substrate is preferably 0.5 to 100 g, more preferably 3 to 50 g.

After applying the semiconductive metal oxide(s) onto the layer obtained in step (i) or (ii), the obtained product is preferably subjected to a heat treatment (sintering step), to electronically contact the metal oxide particles with each other and to increase the coating strength and the adherence thereof with the layer below. The heating temperature is preferably 40 to 700° C., more preferably 100 to 600° C. The heating time is preferably 10 minutes to 10 hours.

However, in case the electrically conductive layer contains a thermosensitive material having a low melting point or softening point such as a polymer film, the product obtained after the application of the semiconductive metal oxide is preferably not subjected to a high temperature treatment because this may damage such a substrate. In this case, the heat treatment is preferably carried out at a temperature as low as possible, for example, 50 to 350° C. In this case, the semiconductive metal oxide is preferably one with smaller particles, in particular having a medium particle size of 5 nm or less. Alternatively, a mineral acid or a metal oxide precursor can be heat-treated at such a low temperature.

Further, the heat treatment may be carried out while applying an ultraviolet radiation, an infrared radiation, a microwave radiation, an electric field, an ultrasonic wave, etc. to the semiconductive metal oxides, in order to reduce the heating temperature. To remove unnecessary organic compounds, etc., the heat treatment is preferably carried out in combination with evacuation, oxygen plasma treatment, washing with pure water, a solvent or a gas, etc.

If desired, it is possible to form a blocking layer on the layer of the semiconductive metal oxide before contacting it with the absorber in order to improve the performance of the semiconductive metal oxide layer. Such a blocking layer is usually introduced after the aforementioned heat treatment. An example of forming a blocking layer is immersing the semiconductive metal oxide layer into a solution of metal alkoxides such as titanium ethoxide, titanium isopropoxide or titanium butoxide, chlorides such as titanium chloride, tin chloride or zinc chloride, nitrides or sulfides and then drying or sintering the substrate. For instance, the blocking layer is made of a metal oxide, e.g. $TiO_2$, $SiO_2$, $Al_2O_3$, $ZrO_2$, MgO, $SnO_2$, ZnO, $Eu_2O_3$, $Nb_2O_5$ or combinations thereof, $TiCl_4$, or a polymer, e.g. poly(phenylene oxide-co-2-allylphenylene oxide) or poly(methylsiloxane). Details of the preparation of such layers are described in, for example, Electrochimica Acta 40, 643, 1995; J. Am. Chem. Soc 125, 475, 2003; Chem. Lett. 35, 252, 2006; J. Phys. Chem. B, 110, 1991, 2006. Preferably, $TiCl_4$ is used. The blocking layer is usually dense and compact, and is usually thinner than the semiconductive metal oxide layer.

(2) Amorphous Material or Composition Comprising Such Material

The amorphous material is preferably adsorbed to a material which has a high surface area. In particular, the amorphous material may be adsorbed to a semiconductive metal oxide.

The amorphous material or a composition comprising such material may be adsorbed to the semiconductive metal oxides by bringing these components into contact with each other, e.g. by soaking the product obtained after the application of the semiconductive metal oxide layer in a solution of the amorphous material or the composition comprising such material, or by applying this solution to the semiconductive metal oxide layer. In the former case, a soaking method, a dipping method, a roller method, an air-knife method, etc. may be used. In the soaking method, the amorphous material or the composition comprising such material may be adsorbed at room temperature, or under reflux while heating as described in JP 7249790. As an applying method of the latter case, a wire-bar method, a slide-hopper method, an extrusion method, a curtain method, a spin method, a spray method, etc. may be used. Further, the amorphous material or the composition may be applied to the semiconductive metal oxide layer by an ink-jet method onto an image, thereby providing a photosensitive layer with a surface having the shape of the image.

If more than one amorphous material or composition comprising such material is to be applied, the application of the two or more amorphous materials or compositions comprising such materials can be carried out simultaneously, e.g. by using a mixture of two or more amorphous materials, or subsequently by applying one amorphous material after the other.

Additionally or alternatively the amorphous material or the composition comprising such material may be applied in combination with the charge transfer material.

(3) Perovskite Absorber Material

In principle, all Perovskite absorber materials known to a person skilled in the art may be employed. The Perovskite absorber material is preferably an organometallic halide compound. Preferred are compounds of the formula $(R^d NH_3)PbX^a{}_3$, wherein $R^d$ is $C_1$-$C_4$ alkyl and $X^a$ is Cl, Br or I. Especially preferred are $(CH_3NH_3)PbI_3$, $(CH_3CH_2NH_3)PbI_3$, $(CH_3NH_3)PbI_2Cl$ and $(CH_3CH_2NH_3)PbI_2Cl$.

(4) Non-Semiconductive Carrier Material

Preferred as a non-semiconductive carrier material is $Al_2O_3$.

(5) Passivating Material

In order to prevent recombination of the electrons in the semiconductive metal oxide with the charge transfer layer a passivating layer can be provided on the semiconductive metal oxide. The passivating layer can be provided before the adsorption of the amorphous material or composition comprising such material, or after the adsorption process. Suitable passivating materials are aluminium salts, $Al_2O_3$, silanes, such as $CH_3SiCl_3$, metal organic complexes, especially $Al^{3+}$ complexes, 4-tert-butyl pyridines, MgO, 4-guanidino butyric acid and hexadecyl malonic acid. The passivating layer is preferably very thin.

(D) Charge Transfer Layer [Step (iv)]

The charge transfer layer may comprise the amorphous material according to the invention or a composition comprising such a material. The charge transfer layer may comprise additional hole-transporting materials.

Suitable additional hole-transporting materials are inorganic hole-transporting materials, organic hole-transporting materials or a combination thereof. Preferably, the additional hole-transporting material is in the solid state. Those compounds are known to a person skilled in the art.

In case the charge transfer layer does not comprise the amorphous material according to the invention or a composition comprising such a material, the hole-transporting material of the photoelectric conversion device is preferably selected from the hole-transporting materials mentioned as additional hole-transporting materials above.

Method for Forming the Charge Transfer Layer:

The charge transfer layer may be provided e.g. by one of the following two methods. According to a first method, the counter electrode is placed on the photosensitive layer first and then the material of the charge transfer layer is applied in the liquid state to penetrate the gap therebetween. According to a second method, the charge transfer layer is first directly disposed on the photosensitive layer and the counter electrode is disposed afterwards.

In the case of providing a wet charge transfer layer by the second method, the wet charge transfer layer is applied to the photosensitive layer, the counter electrode is disposed on the wet charge transfer layer without drying it and edges thereof are subjected to a treatment for preventing liquid-leakage, if necessary. In the case of providing a gel charge transfer layer by the second method, the charge transfer material may be applied in the liquid state and gelled by polymerization, etc. In this case, the counter electrode may be disposed on the charge transfer layer before or after drying and fixing the charge transfer layer.

The charge transfer layer may be disposed e.g. by a roller method, a dip method, an air-knife method, an extrusion method, a slide-hopper method, a wire-bar method, a spin method, a spray method, a cast method or a printing method. Suitable methods are similar to those of forming the semiconductive metal oxide layer or adsorbing the amorphous material to the semiconductor, mentioned above.

If the charge transfer layer is composed of at least one solid electrolyte, the solid hole transporting material, etc. may be formed by a dry film-forming method such as a physical vacuum deposition method or a CVD method, followed by disposing the counter electrode thereon. The hole-transporting material may be made to penetrate into the photosensitive layer by a vacuum deposition method, a cast method, a coating method, a spin-coating method, a soaking method, an electrolytic polymerization method, a photopolymerization method, a combination of these methods, etc.

(E) Counter Electrode [Step (v)]

As already said, the counter electrode is the counter electrically conductive layer, which is optionally supported by a substrate as defined above. Examples of the electrically conductive material used for the counter electrically conductive layer include: metals such as platinum, gold, silver, copper, aluminum, magnesium and indium; mixtures and alloys thereof, especially of aluminum and silver; carbon; electrically conductive metal oxides such as indium-tin composite oxides and fluorine-doped tin oxides. Among them, preferred are platinum, gold, silver, copper, aluminum and magnesium, and particularly preferred silver or gold. Specifically, silver is used. Suitable electrodes are moreover mixed inorganic/organic electrodes and polylayer electrodes, such as LiF/Al electrodes. Suitable electrodes are described for example in WO 02/101838 (especially pp 18-20).

The substrate of the counter electrode is preferably made of a glass or a plastic to be coated or vapor-deposited with the electrically conductive material. The counter electrically conductive layer preferably has a thickness of 3 nm to 10 μm, although the thickness is not particularly limited.

Light may be irradiated from any one or both sides of the electrically conductive layer provided in step (i) and the counter electrode provided in step (v), so that at least one of them should be substantially transparent to have light reached to the photosensitive layer. From a viewpoint of improving electric generation efficiency, it is preferable that the electrically conductive layer provided in step (i) is substantially transparent to incident light. In this case, the counter electrode preferably has a light-reflective property. Such a counter electrode may be composed of a glass or a plastic having a vapor-deposited layer of metal or electrically conductive oxide, or metal thin film. This type of device, which is also called "concentrator", is described for example in WO 02/101838 (especially on pp 23-24).

The counter electrode may be disposed by applying metal-plating or vapor-depositing (physical vapor deposition (PVD), CVD, etc.) the electrically conductive material directly onto the charge transfer layer. Similar as with the conductive support, it is preferable that a metal lead is used to reduce the resistance of the counter electrode. The metal lead is particularly preferably used for a transparent counter electrode. Preferable embodiments of the metal lead used for the counter electrode are the same as those of the metal lead used for the conductive layer mentioned above.

(F) Others

At least one further functional layer, such as a protective layer and a reflection-preventing layer, may be disposed on any one or both of the conductive layers and/or the counter electrode. The functional layers may be disposed by a method selected in accordance with the materials used therefor, such as a coating method, a vapor-deposition method and a sticking method.

(G) Interior Structure of the Photoelectric Conversion Device

The photoelectric conversion device may have various interior structures according to the desired end use. The structures are classified into two major forms, a structure allowing light incidence from both faces, and a structure allowing it from only one face. In the first case, the photosensitive layer, the charge transfer layer and the other optionally present layers are disposed between a transparent electrically conductive layer and a transparent counter electrically conductive layer. This structure allows light incidence from both faces of the device. In the second case, one of the transparent electrically conductive layer and the transparent counter electrically conductive layer is transparent, while the other is not. As a matter of course, if the electrically conductive layer is transparent, light immerses from the electrically conductive layer side, while in case of the counter electrically conductive layer being transparent, light immerses from the counter electrode side.

Preferably, the photoelectric conversion device of the invention is part of a photoelectric cell, more preferably a solar cell.

A photoelectric cell is constituted by connecting a photoelectric conversion device to an external circuit to electrically work or generate electricity in the external circuit. Such a photoelectric cell that has a charge transfer layer composed of ion conductive material is referred to as a photo-electrochemical cell. A photoelectric cell intended for power generation using solar light is referred to as a solar cell.

Thus, a photoelectric cell is constituted by connecting the photoelectric conversion device of the present invention to an external circuit to electrically work or generate electricity in the external circuit. Preferably, the photoelectric cell is a solar cell, i.e. a cell intended for power generation using solar light.

The side face of the photoelectric cell is preferably sealed with a polymer or an adhesive agent, etc. to prevent deterioration and volatility of the content in the cell. The external circuit is connected to the conductive support and the counter electrode via a lead. Various known circuits may be used in the present invention.

In the case where the photoelectric conversion device of the present invention is applied to the solar cell, the interior structure of the solar cell may be essentially the same as that of the photoelectric conversion device mentioned above. The solar cell comprising the photoelectric conversion device of the present invention may have a known module structure. In generally known module structures of solar cells, the cell is placed on a substrate of metal, ceramic, etc. and covered with a coating resin, a protective glass, etc., whereby light is introduced from the opposite side of the substrate. The solar cell module may have a structure where the cells are placed on a substrate of a transparent material such as a tempered glass to introduce light from the transparent substrate side. Specifically, a super-straight type module structure, a substrate type module structure, a potting type module structure, substrate-integrated type module structure that is generally used in amorphous silicon solar cells, etc. are known as the solar cell module structures. The solar cell comprising the photoelectric conversion device of the present invention may have a module structure which is properly selected e.g. from the above structures which may be adapted in accordance with the respective requirements of a specific use.

The solar cell of the invention may be used in a tandem cell. Thus, the invention also relates to a tandem cell comprising the solar cell of the invention and an organic solar cell.

Tandem cells are principally known and are described for example in WO 2009/013282. The tandem cells of the invention may be made as those described in WO 2009/013282, where the solar cell of the invention however replaces the dye-sensitized solar cell described in this reference.

The amorphous materials of the invention or compositions comprising such materials are advantageously suitable for field-effect transistors (FETs). They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. For the production of semiconductor materials, the amorphous material of the invention can be processed further by one of the following processes: printing (offset, flexographic, gravure, screen-printing, inkjet, electrophotography), laser transfer, photolithography, drop-casting. They are especially suitable for use in displays (specifically large-surface area and/or flexible displays), RFID tags, smart labels and sensors.

The amorphous materials of the invention or compositions comprising such materials are also advantageously suitable as electron conductors in field-effect transistors (FETs), photoelectric conversion devices, in particular solar cells, and in light-emitting diodes (LEDs). They are also particularly advantageous as an exciton transport material in excitonic solar cells.

The invention further relates to field-effect transistors comprising a substrate with at least one gate structure, a source electrode and a drain electrode, and at least one amorphous material according to the invention or a composition comprising such a material as a semiconductor.

The invention further relates to substrates having a plurality of field-effect transistors, wherein at least some of the field-effect transistors comprise at least one amorphous material according to the invention or a composition comprising such a material.

The invention further provides an electroluminescent (EL) arrangement comprising an upper electrode, a lower electrode, wherein at least one of said electrodes is transparent, an electroluminescent layer and optionally an auxiliary layer, wherein the electroluminescent arrangement comprises at least one amorphous material of the invention or a composition comprising such a material. An EL arrangement is characterized by the fact that it emits light when an electrical voltage is applied with flow of current. Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and light-emitting diode (LEDs) are used synonymously. As a rule, EL arrangements are constructed from several layers. At least one of those layers contains one or more charge transport elements. The layer structure is in principle as follows:

1. Carrier, substrate
2. Base electrode (anode)
3. Hole-injecting layer
4. Hole-transporting layer
5. Light-emitting layer
6. Electron-transporting layer
7. Electron-injecting layer
8. Top electrode (cathode)
9. Contacts
10. Covering, encapsulation.

This structure represents the most general case and can be simplified by omitting individual layers, so that one layer performs several tasks. In the simplest case an EL arrangement consists of two electrodes between which an organic layer is arranged, which fulfills all functions, including emission of light. The structure of light-emitting diodes and processes for their production are analogous to those of organic light-emitting diodes (OLEDs). These structures and processes for their production are principally known to those skilled in the art, for example from WO 2005/019373. Suitable materials for the individual layers of LEDs are disclosed, for example, in WO 00/70655. Reference is made here to the disclosure of these documents. In principle LEDs according to the invention can be produced by methods known to those skilled in the art. In a first embodiment, an LED is produced by successive vapor deposition of the individual layers onto a suitable substrate. For vapor deposition, it is possible to use customary techniques such as thermal evaporation, chemical vapor deposition and others. In an alternative embodiment, the layers, in particular the amorphous material of the invention or a composition comprising such a material, may be coated from solutions or dispersions in suitable solvents, for which coating techniques known to those skilled in the art are employed.

The amorphous materials of the invention or compositions comprising such materials are advantageously suitable for thin film transistors (TFTs). In order to provide the thin film transistors, the amorphous materials of the invention or the composition comprising such materials is preferably processed further by one of the following processes: printing (offset, flexographic, gravure, screenprinting, inkjet, electrophotography), laser transfer, photolithography, drop-casting.

The amorphous materials of the invention are also advantageously suitable in light-emitting diodes (LEDs), in particular as or in the semiconducting layers of light-emitting diodes. The amorphous materials of the invention are also particularly suitable as or in the phosphor materials of the light-emitting diodes.

The amorphous materials of the invention are particularly suitable as charge transport materials. In particular, the amorphous materials of the invention are suitable as charge transport materials in batteries. The amorphous materials of the invention are also particularly suitable as charge transport materials in rechargeable batteries (accumulators).

The invention is illustrated in detail with reference to the following nonrestrictive examples.

EXAMPLES

Crystalline compounds in the educt and product mixtures were identified by X-ray powder diffractometry recorded at 25° C. using Cu-Kα radiation (1.54178 Å).

The melting behaviour of the educt and product mixtures was determined by differential scanning calorimetry (DSC) under a nitrogen atmosphere at a heating rate of 20 K/min in aluminium crucibles.

Figure 1:
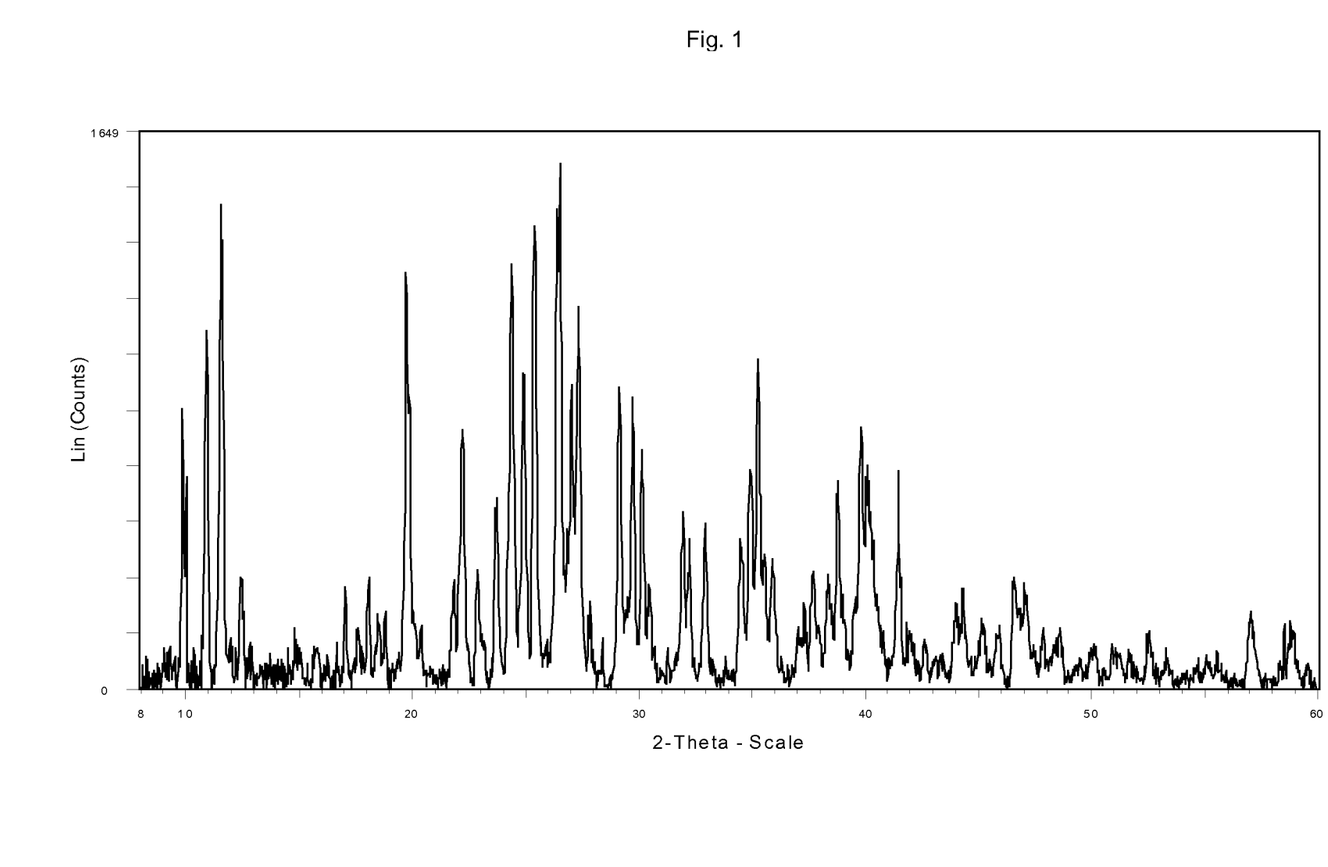
FIG. 1 shows the XRD of the educt mixture at ambient temperature (20° C.) before heating.
Figure 2:
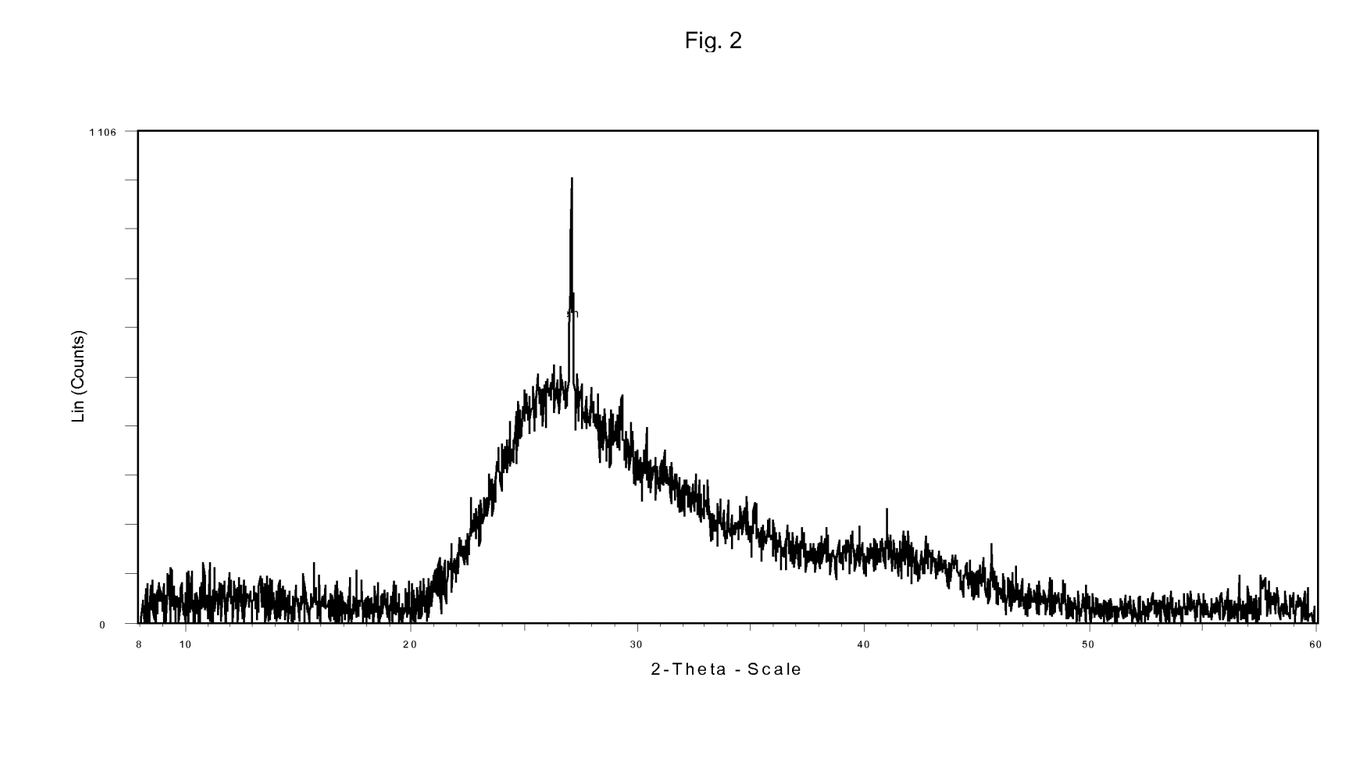
FIG. 2 shows the XRD of the reaction mixture at 140° C. wherein no reflexes are visible, indicating the melt.

In a 100 mL reaction vessel, 3 g CH$_3$NH$_3$I, 0.546 g CH$_3$NH$_3$Cl and 1.499 g PbCl$_2$ (molar ratios: 3.5:1.5:1) were heated under nitrogen atmosphere (heating rate: 20° C./min) to a temperature of 140°. The reaction mixture was then allowed to cool to ambient temperature (20° C.). Temperature depending XRD measurements were carried out. FIG. 1 shows the XRD of the educt mixture at ambient temperature (20° C.) before heating. At 140° C., a clear yellow-colored melt without solid contents was obtained. FIG. 2 shows the XRD of the reaction mixture at 140° C. wherein no reflexes are visible, indicating the melt.

Figure 3:
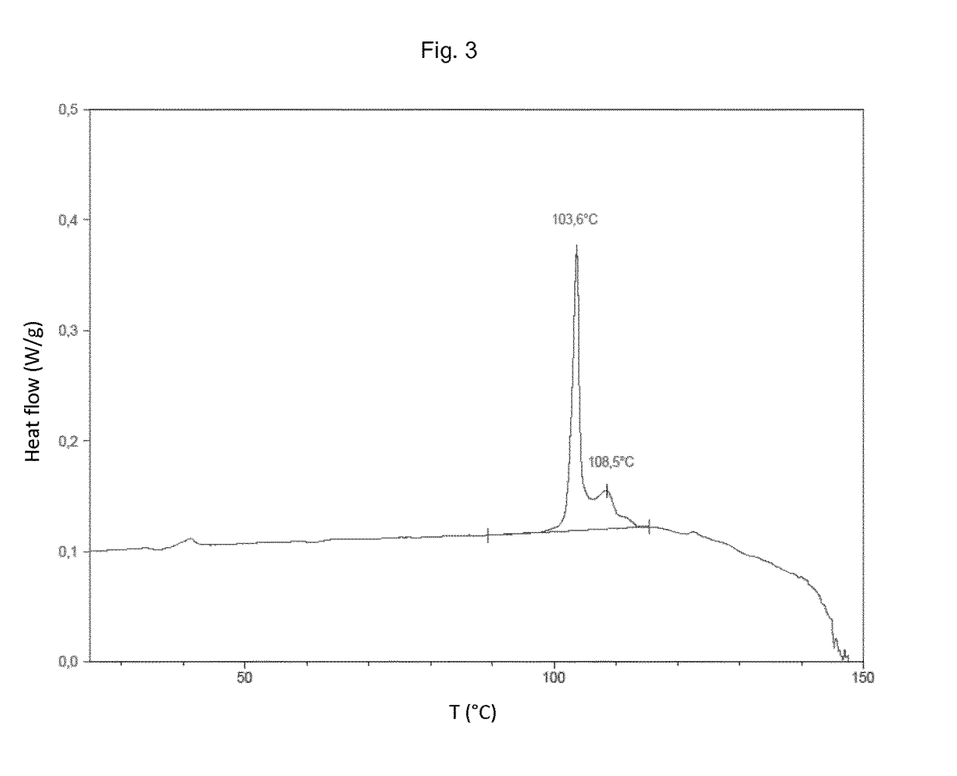
FIG. 3 shows the DSC measurement that confirms the thermal behavior and also shows no mass loss. The amorphous material was stable under inert atmosphere.

The obtained product was analyzed by DSC and XRD measurements. Surprisingly the product showed a low melting point of about 100° C. (melting points of the educts: CH$_3$NH$_3$I=240° C., CH$_3$NH$_3$Cl=230° C., PbCl$_2$=500° C.). This low melting point is in conformity with the observation that the main product is an amorphous material with the composition 5 (CH$_3$NH$_3$) 1 Pb 3.5 I 3.5 Cl according to the elementary analysis. No mass loss was observed during the reaction. FIG. 3 shows the DSC measurement that confirms the thermal behavior and also shows no mass loss. The amorphous material was stable under inert atmosphere.

Beside the solid state synthesis, it was possible to prepare a solution of the educts or the amorphous compound in dimethylformamide (or other polar organic solvents) that is also a suitable solvent for the amorphous compound. The reaction mixture was heated to 60° C. and kept under reflux for 1 hour. After evaporation of the solvents the behavior was similar to the solid state synthesis, i.e. an amorphous phase was present with a low melting point of approx. 100° C.

A similar behavior was observed by substituting Pb with Sn. With the same molar ratios (5:1:3.5:3.5, CH$_3$NH$_3$:Sn:I:Cl) after heating to 120° C. an amorphous material with a low melting point was obtained. The melting point of this mixture was detected via DSC measurement. The mixture started to melt above 70° C. and again no mass loss was observed.

The invention claimed is:

1. An amorphous material having a composition $$(R^1NR^2_3)_5MeX^1_aX^2_b$$

wherein
R$^1$ is C$_1$-C$_4$-alkyl,
R$^2$ are independently of one another hydrogen or C$_1$-C$_4$-alkyl,
Me is a divalent metal,
X$^1$ and X$^2$ are different from each other, and are independently of one another selected from the group consisting of F, Cl, Br, I, CN, SCN, OCN, and N$_3$, and
a and b are independently of one another 0 to 7, wherein the sum of a and b is 7.

2. The amorphous material according to claim 1, wherein R$^1$ is methyl or ethyl.

3. The amorphous material according to claim 1, wherein the R$^2$ groups are all hydrogen.

4. The amorphous material according to claim 1, wherein Me is at least one element selected from the group consisting of Pb, Sn, Fe, Zn, Cd, Co, Cu, Ni, and Mn.

5. The amorphous material according to claim 1, wherein Me is Pb or Sn.

6. The amorphous material according to claim 1, wherein X$^1$ is I and X$^2$ is Cl.

7. The amorphous material according to claim 1, wherein a and b are both 3.5.

8. An amorphous material having a composition $$(CH_3NH_3)_5PbI_{3.5}Cl_{3.5}$$

or $$(CH_3NH_3)_5SnI_{3.5}Cl_{3.5}.$$

9. A composition comprising the amorphous material of claim 1.

10. A process for preparing an amorphous material having a composition $$(R^1NR^2_3)_5MeX^1_aX^2_b$$

wherein
R$^1$ is C$_1$-C$_4$-alkyl,
R$^2$ are independently of one another hydrogen or C$_1$-C$_4$-alkyl,
Me is a divalent metal,
X$^1$ and X$^2$ are different from each other, and are independently of one another selected from the group consisting of F, Cl, Br, I, CN, SCN, OCN, and N$_3$,
a and b are independently of one another 0 to 7, wherein the sum of a and b is 7,
the process comprising reacting
a compound having a formula (R$^1$NR$^2_3$)X$^1$,
a compound having a formula (R$^1$NR$^2_3$)X$^2$ and
a compound having a formula MeX$^2_2$,
at an elevated temperature in a melt or in the presence of a solvent.

11. The process according to claim 10, wherein the compounds are mixed in a ratio that corresponds to the stoichiometric amount of the elements in the composition $$5(R^1NR^2_3):1Me:aX^1:bX^2.$$

12. The process according to claim 10, wherein molar ratios of (R$^1$NR$^2_3$)X$^1$:(R$^1$NR$^2_3$)X$^2$:MeX$^2_2$ are about 3.5:1.5:1.

13. The process according to claim 10, that produces an amorphous material having a composition (CH$_3$NH$_3$)$_5$ Pb I$_{3.5}$Cl$_{3.5}$ comprising reacting (CH$_3$NH$_3$)I, (CH$_3$NH$_3$)Cl and PbCl$_2$.

14. The process according to claim 10, that produces an amorphous material having a composition (CH$_3$NH$_3$)$_5$ Sn I$_{3.5}$ Cl$_{3.5}$ comprising reacting (CH$_3$NH$_3$)I, (CH$_3$NH$_3$)Cl and SnCl$_2$.

15. A photoelectric conversion device comprising the amorphous material of claim 1.

16. The photoelectric conversion device according to claim 15, further comprising:
an electrically conductive layer being part of or forming a working electrode,
a photosensitive layer comprising an absorber material and optionally comprising a semi-conductive metal oxide or an insulating material,
a charge transfer layer, and
an electrically conductive layer being part of or forming a counter electrode,
wherein the photosensitive layer and/or the charge transfer layer comprises the amorphous material.

17. The photoelectric conversion device according to claim 16, wherein the photosensitive layer comprises the amorphous material as an absorber material.

18. The photoelectric conversion device according to claim 16, wherein the photosensitive layer comprises a Perovskite material as an absorber material.

19. The photoelectric conversion device according to claim 16, further comprising a hole-conducting layer between the charge transfer layer and the counter electrode.

20. A solar cell comprising the photoelectric conversion device according to claim 15.

21. A field-effect transistor (FET), comprising a substrate comprising a gate structure, a source electrode and a drain electrode and the amorphous material of claim 1.

22. A substrate comprising a plurality of field-effect transistors, wherein at least some of the field-effect transistors comprise the amorphous material of claim 1.

23. An electroluminescent arrangement comprising an upper electrode, a lower electrode, wherein at least one of the electrodes is transparent, an electroluminescent layer and optionally an auxiliary layer, wherein the electroluminescent arrangement comprises the amorphous material of claim 1.

24. The electroluminescent arrangement of claim 23 in a form of a light-emitting diode (LED).

25. A semiconducting layer of a thin film transistor (TFT), a semiconducting layer of a light emitting diode (LED), a phosphor material of an LED, or a charge transport material of a battery, comprising the amorphous material of claim 1.

26. The amorphous material according to claim 1, wherein:
   $X^1$ and $X^2$ are different from each other, and are independently of one another selected from the group consisting of CN, SCN, OCN, and $N_3$.

27. The amorphous material according to claim 1, wherein:
   $X^1$ and $X^2$ are different from each other, and are independently of one another selected from the group consisting of F, Cl, Br, and I.

28. The amorphous material according to claim 8, having a composition $(CH_3NH_3)_5Pb\ I_{3.5}\ Cl_{3.5}$.

29. The amorphous material according to claim 8, having a composition $(CH_3NH_3)_5\ Sn\ I_{3.5}\ Cl_{3.5}$.

* * * * *

UNITED STATES PATENT AND TRADEMARK OFFICE
CERTIFICATE OF CORRECTION

PATENT NO. : 10,347,848 B2  
APPLICATION NO. : 14/916523  
DATED : July 9, 2019  
INVENTOR(S) : Wilfried Hermes et al.

Page 1 of 1

It is certified that error appears in the above-identified patent and that said Letters Patent is hereby corrected as shown below:

On the Title Page

In Column 2, item (57), Abstract, Line 5, "$(R^1NR^2{}_3)_5Me\ X^1{}_aX^2{}_b$" should read -- $(R^1NR^2{}_3)_5MeX^1{}_aX^2{}_b$ --

In the Claims

In Column 18, Lines 41-42, Claim 13, "$(CH_3NH_3)_5\ Pb\ I_{3.5}Cl_{3.5}$" should read -- $(CH_3NH_3)_5PbI_{3.5}Cl_{3.5}$ --

In Column 18, Lines 45-46, Claim 14, "$(CH_3NH_3)_5\ Sn\ I_{3.5}\ Cl_{3.5}$" should read -- $(CH_3NH_3)_5SnI_{3.5}Cl_{3.5}$ --

In Column 20, Line 16, Claim 28, "$(CH_3NH_3)_5Pb\ I_{3.5}\ Cl_{3.5}.$" should read -- $(CH_3NH_3)_5PbI_{3.5}Cl_{3.5}.$ --

In Column 20, Line 18, Claim 29, "$(CH_3NH_3)_5\ Sn\ I_{3.5}\ Cl_{3.5}.$" should read -- $(CH_3NH_3)_5SnI_{3.5}Cl_{3.5}.$ --

Signed and Sealed this  
Seventh Day of April, 2020

Andrei Iancu  
*Director of the United States Patent and Trademark Office*